(12) United States Patent
Kalloo et al.

(10) Patent No.: US 10,722,221 B2
(45) Date of Patent: Jul. 28, 2020

(54) METHOD AND DEVICE FOR STATISTICAL TISSUE SAMPLING USING MICRODEVICES

(71) Applicant: The Johns Hopkins University, Baltimore, MD (US)

(72) Inventors: Anthony N. Kalloo, Baltimore, MD (US); David H. Gracias, Baltimore, MD (US); Florin M. Selaru, Catonsville, MD (US); Evin Gultepe, Baltimore, MD (US); Mouen A. Khashab, Towson, MD (US)

(73) Assignee: The Johns Hopkins University, Baltimore, MD (US)

(*) Notice: Subject to any disclaimer, the term of this patent is extended or adjusted under 35 U.S.C. 154(b) by 273 days.

(21) Appl. No.: 15/665,066

(22) Filed: Jul. 31, 2017

(65) Prior Publication Data

US 2018/0028165 A1    Feb. 1, 2018

Related U.S. Application Data

(62) Division of application No. 14/114,741, filed as application No. PCT/US2012/036386 on May 3, 2012, now Pat. No. 9,717,484.

(60) Provisional application No. 61/541,962, filed on Sep. 30, 2011, provisional application No. 61/525,364, filed on Aug. 19, 2011, provisional application No. 61/483,536, filed on May 6, 2011.

(51) Int. Cl.
*A61B 5/00* (2006.01)
*A61B 10/04* (2006.01)
*A61B 10/02* (2006.01)
*A61B 17/00* (2006.01)

(52) U.S. Cl.
CPC .............. *A61B 10/04* (2013.01); *A61B 10/02* (2013.01); *A61B 2017/00345* (2013.01); *A61B 2017/00876* (2013.01)

(58) Field of Classification Search
CPC .................... A61B 10/02; A61B 10/04; A61B 2017/00345; A61B 2017/00876
See application file for complete search history.

(56) References Cited

U.S. PATENT DOCUMENTS

| | | |
|---|---|---|
| 7,309,316 B1 | 12/2007 | Flynn |
| 7,390,324 B2 | 6/2008 | Whalen |
| 8,668,654 B1 * | 3/2014 | Gerrans ................. A61B 10/02 600/562 |
| 8,703,073 B2 | 4/2014 | Gracias |
| 9,128,084 B2 | 9/2015 | Prins |
| 2002/0133115 A1 | 9/2002 | Gordon et al. |
| 2004/0015155 A1 | 1/2004 | Whalen |
| 2007/0060838 A1 | 3/2007 | Dib |
| 2010/0009456 A1 | 1/2010 | Prins |
| 2010/0326071 A1 | 12/2010 | Gracias |

FOREIGN PATENT DOCUMENTS

WO    WO 2009/111737 A1    9/2009

* cited by examiner

*Primary Examiner* — Max F Hindenburg
(74) *Attorney, Agent, or Firm* — DLA Piper LLP (US)

(57) ABSTRACT

The present invention utilizes tetherless microtools to biopsy tissue. The invention provides a device and method for deployment and retrieval of tetherless microtools. The size of the microtools ensures that tissue damage at a site targeted for biopsy is negligible. As such, large numbers of microtools may be deployed ensuring that a true statistical sampling of biologic tissue is performed.

8 Claims, 8 Drawing Sheets

THROUGH THE SCOPE ANCHORING BALLOON,
OVER THE CATHETER RETRIEVAL TOOL

1. CATHETER WITH INFLATABLE BALLOON AT TIP-PASSED THROUGH SCOPE AND INFLATED AT DISTAL/DESIRED LOCATION →ANCHORED

2. SCOPE REMOVED LEAVING IN PLACE ANCHORED BALLOON

3. MAGNETIC TOOL PASSED OVER CATHETER

INFLATABLE PORTION OF MAGNETIC RETRIEVAL TOOL

MAGNETIC STRIPS

4. ONCE TIP OF MAGNETIC TOOL REACHES ANCHORING BALLOON→ANCHORING BALLOON DEFLATED; MAGNETIC PORTION OF TOOL INFLATED→
BOTH ANCHORING BALLOON & MAGNETIC TOOL RETRIEVED SIMULTANEOUSLY

RETRIEVED GRIPPERS ON THE MAGNET

FIG. 13A open
FIG. 13B closed
FIG. 13C re-opened
FIG. 13D
FIG. 13E Enzyme 1
FIG. 13F Enzyme 2
FIG. 13G
FIG. 13H
FIG. 13I Cr  Au  Ni  Biopolymer 1 intact  Biopolymer 1 degraded  Biopolymer 2 intact  Biopolymer 2 degraded

FIG. 14

METHOD AND DEVICE FOR STATISTICAL TISSUE SAMPLING USING MICRODEVICES

CROSS-REFERENCE TO RELATED APPLICATIONS

This application is a divisional application of U.S. application Ser. No. 14/114,741 filed Apr. 3, 2014, now issued as U.S. Pat. No. 9,717,484; which is a 35 USC § 371 National Stage application of International Application No. PCT/US2012/036386 filed May 3, 2012, now expired; which claims the benefit under 35 USC § 119(e) to U.S. Application Ser. No. 61/541,962 filed Sep. 30, 2011, U.S. Application Ser. No. 61/525,364 filed Aug. 19, 2011 and U.S. Application Ser. No. 61/483,536 filed May 6, 2011, all now expired. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under Grant No. DP2-OD 004346-01 awarded by the National Institutes of Health. The government has certain rights in the invention.

BACKGROUND OF THE INVENTION

Field of the Invention

The present invention relates generally to diagnostics and more specifically to a method and device for obtaining randomized tissue samples for statistical sampling and analysis for diagnostic and prognostic evaluations.

Background Information

Over the past several years, numerous genetic and epigenetic alterations were identified in a wide variety of disorders. In cancer, in particular, multiple alterations of etiologic and/or diagnostic values have been identified. Gene expression studies have identified single genes, or panels of genes to accurately diagnose normal, pre-malignant or malignant lesions, as well as to differentiate between subtypes of cancer. In addition to mRNA species, micro-RNA (miRNA) alterations have been determined to be associated with various inflammatory or malignant conditions, and can be used for diagnostic purposes. Epigenetic alterations have also been shown to be predictive of malignant transformation.

The diagnostic accuracy of various tests based on genetic or epigenetic alterations in particular, and histological analysis in general, is, however, intrinsically linked to the quality and volume of tissue that is available for analysis. As such, obtaining the relevant tissue is essential for the diagnosis.

Well executed tissue sampling procedures are especially crucial for biopsy of potential mucosal abnormalities in the gastrointestinal (GI) tract and elsewhere in the body that cannot be readily diagnosed based on their appearance on visual observation; e.g., during endoscopic examination. For example, several patchy conditions of the stomach, including infection with *Helicobacter Pylori*, autoimmune atrophic gastritis and dysplasia, mandate obtaining biopsies at several locations in the stomach. Similarly, biopsy-based diagnosis of microscopic colitis, dysplasia in ulcerative colitis, and others mandate obtaining multiple biopsies.

With the recent advent of endoscopy and laparoscopy, access to the inside of the human body has become routine. However, visual inspection is continually relied upon to aid diagnosis by obtaining tissue biopsy with tethered and relatively large biopsy forceps devices. Space limitations, time limitations and tissue damage limitations all contribute to dismal ability of performing a true statistical sampling of biologic tissue.

A key step to increase the number of biopsy sites while preventing unnecessary tissue damage is the miniaturization of the biopsy tools. Smaller tools are being developed for use at different biopsy sites to minimize tissue loss. However, they remain limited in application to the confined, low visibility environment of bodily passages.

SUMMARY OF THE INVENTION

The present invention provides a clinically appropriate method for biopsying tissue in difficult to access regions of a human or animal body. According to the method, a plurality of tetherless microtools is deployed to tissue targeted for biopsy. A clinically useful method for retrieval of the microtools with the tissue samples is also provided.

The nanoscale size of microtools suitable for use in the invention ensures that tissue damage at the deployment site is negligible. As such, large numbers of microtools may be deployed in numbers sufficient to enable statistically significant sampling of the targeted tissue. In a preferred embodiment, the microtools are adapted to open and close around targeted tissue in response to specific stimuli such as temperature, allowing them to be used without need for additional biopsy instruments.

In another aspect, the present invention provides a method for deployment of a tetherless microtool into a cavity of a subject. The method includes: a) introducing a device comprising one or more magnets into a cavity of a subject; and b) deploying a tetherless microtool magnetically detachable from the one or more magnets to a tissue of the cavity.

In one aspect, the present invention provides a method of tissue sampling. The method includes: a) contacting a plurality of tetherless microtools with a tissue of a subject, each microtool having a first configuration; b) allowing the plurality of tetherless microtools to alter from the first configuration to a second configuration while in contact with the tissue, the second configuration adapted such that each microtool grasps the tissue at a discrete location; and, c) retrieving the plurality of tetherless microtools from the subject using a device comprising one or more magnets, wherein each microtool retains an individual sample of the tissue upon retrieval, thereby performing tissue sampling.

In another aspect, the present invention provides a method for retrieval of a tetherless microtool from a subject. The method includes: a) introducing a device comprising one or more magnets into a bodily cavity of the subject, the cavity defining or being adjacent to tissue having at least one tetherless microtool attached thereto, wherein the microtool is comprised in whole or in part of a magnetically responsive material; b) allowing the one or more magnets of the device to contact the tetherless microtool; and c) retrieving the tetherless microtool from the subject via magnetism by removing the device from the cavity, wherein the microtool retains a tissue sample from the cavity upon retrieval.

In yet another aspect, the present invention provides a method of obtaining a randomized tissue sample during a diagnostic biopsy of a subject using tetherless microtools and the device of the present invention. The method includes: a) introducing a plurality of tetherless microtools into a cavity of a subject; b) introducing a device comprising an expandable element having one or more magnets into the cavity; c) anchoring the device via the expandable element so as to facilitate contact between the expandable element and the plurality of tetherless microtools; d) withdrawing the device so that the plurality of tetherless microtools collect on the expandable element via magnetism and are removed from the subject, wherein each of the plurality of tetherless microtools comprise an individual tissue sample from the cavity; and e) processing the samples for diagnostic or prognostic biopsy.

In another aspect, the present invention provides a device for deployment or retrieval of a tetherless microtool from a subject. The device includes one or more magnets configured for retrieval or deployment of a magnetically responsive tetherless microtool. A system for biopsy use including the device further including a tetherless microtool magnetically detachable to the one or more magnets.

In various embodiments, the tetherless microtools are deployed and/or retrieved from the subject using the device of the present invention. In certain such embodiments, the device is configured as a catheter having one or more openings in the elongated shaft of the device for deployment of the plurality of tetherless microtools. In some embodiments, the shaft of the device further includes a main lumen extending the entire length of the shaft which is configured to allow passage therethrough of an endoscope or a catheter.

In some embodiments, the device further comprises an expandable element. In certain of these embodiments, the expandable element is an inflatable balloon, resilient coil, stent or spring. If a balloon, device may be configured as a balloon catheter. In some embodiments thereof, magnets are disposed on the expandable element, and may be integrated therein (e.g., within or as the material forming a coil, stent or spring) or provided thereon as dots or strips (e.g., on the outer surface of a balloon). In some embodiments, the expandable element is disposed at the distal end of the catheter shaft to provide ready contact between the magnets and deployed microtools.

In alternative embodiments, the tetherless microtools are constructed in whole or in part of bioresorbable materials. As such, if left behind in the body (whether intentionally or inadvertently), they will eventually become absorbed.

In various embodiments, the method further includes analyzing the individual samples retrieved from the tetherless microtools. For example, the analysis may include analysis of one or more nucleic acid sequences, e.g., genetic analysis, to diagnose a disease or condition.

In another aspect, the present invention provides a method of diagnosing a condition or disease in a subject. The method includes: a) obtaining a tissue sample from a subject via the method of the invention; b) analyzing the tissue sample; and c) providing a diagnosis of the condition or disease based on the analysis.

In another aspect, the present invention provides a method of providing a prognosis for a condition or disease in a subject. The method includes: a) obtaining a tissue sample from a subject via the method of the invention; b) analyzing the tissue sample; and c) providing a prognosis of the condition or disease based on the analysis.

BRIEF DESCRIPTION OF THE DRAWINGS

FIGS. 1A-1H provide a series of schematic representations depicting fabrication and operation of a microtool, configured as a microgripper, in one embodiment of the invention.

FIGS. 2A-2I provide images showing capture and retrieval of cells using microgrippers depicted in FIG. 1A-FIG. 1H in one embodiment of the invention. The scale bar is 1 mm long.

FIGS. 8A-8B provide pictorial representations of an ex-vivo colonoscopy performed on porcine colon.

FIGS. 9A-9D provide pictorial representations of deployment and retrieval of the microgrippers in an ex-vivo porcine model in one embodiment of the invention.

FIGS. 10A-10D provide pictorial representations including optical microscopy images and gel electrophoresis results of tissue obtained using microgrippers.

FIGS. 12A-12B provide pictorial representations of optical microscopy images.

FIGS. 13A-13I provide schematic representations depicting fabrication and operation of a microgripper in one embodiment of the invention that can close and re-open on exposure to enzymes. FIGS. 13A-13C are optical images of the grippers in the flat, closed, and re-opened states respectively. The arrow indicates the second set of hinges. Scale bars represent 200 µm. FIGS. 13D and 13F are schematic representations of the microgrippers in the three corresponding states above. In FIG. 13D the gripper is held flat by the thick, crosslinked biopolymer (hatching). When the biopolymer is selectively degraded by enzyme 1 the modulus decreases and the gripper closes. In FIG. 13F, the second trigger, a rigid biopolymer insensitive to enzyme 1, is preventing a second set of hinges from actuating, keeping the gripper closed. Subsequently this trigger can be actuated by enzyme 2 to re-open the gripper. FIGS. 13G-13I are cross sectional views of a magnified single hinge illustrating behavior of biopolymer trigger. FIG. 13G shows that both biopolymer layers are stiff, preventing all bending. FIG. 13G shows that on degrading the biopolymer with enzyme 1, the second hinge remains flat. FIG. 13I shows that when the second polymer is degraded by enzyme 2 the hinge bends in the opposite direction.

DETAILED DESCRIPTION OF THE INVENTION

The present invention provides a method and device for performing tissue sampling utilizing a plurality of microdevices or microtools in a tetherless fashion. As discussed herein, microtools useful in the invention are relatively non-invasive and non-toxic devices. According to the invention, microtools are deployed in numbers sufficient to greatly improve statistical sampling of biologic tissue and retrieved to perform a molecular and/or histological diagnostic assay of enhanced sensitivity compared to analysis of conventionally obtained biopsy samples.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention provides an innovative biopsying technique that provides significantly improved tissue sampling. The invention is centered on the development of tetherless microtools, or microgrippers, that are deployed to a tissue via an invasive scope, such as an endoscope or laparoscope. After deployment, the microtools are activated intraluminally to capture a plurality of tissue samples. The microtools, with tissue samples joined thereto, are then retrieved for analysis using a retrieval device as described herein.

As used herein, the term "microtool" is used synonymously with the terms "microgripper" or "gripper" and is intended to refer to a device having multiple layers configured to allow for the structural configuration of the device to change from in a first configuration to a second configuration in response to a stimulus, such as a change in a local environmental condition. Change from the first configuration to the second configuration allows for the device to grasp tissue via release of stored torsional energy in one or more layers of the device.

More specifically, microgrippers for use with the present invention are generally lithographically structured devices having an actuation layer and a control layer operatively connected to the actuation layer. The actuation layer includes a stress layer and a neutral layer that is constructed of materials and with a structure such that it stores torsional energy upon being constructed. The control layer is constructed to maintain the actuation layer substantially in a first configuration in a local environmental condition and is responsive to a change in the local environmental condition such that it permits a release of stored torsional energy to cause a change in a structural configuration of the lithographically structured device to a second configuration, the control layer thereby providing a trigger mechanism.

Preferred microgrippers for use with the present invention are disclosed in International Publication No. WO 2009/111737, the entire contents of which are incorporated herein by reference. Additional microgrippers for use with the present invention are disclosed in Bassik et al. (*J Am Chem Soc* 132:16314-7 (2010)), Leong et al. (*Proc Natl Acad Sci USA* 106:703-8 (2009)) and Randhawa et al. (*J Am Chem Soc* 130:17238-9 (2008)), the entire contents of which are also incorporated herein by reference.

Figure 4:
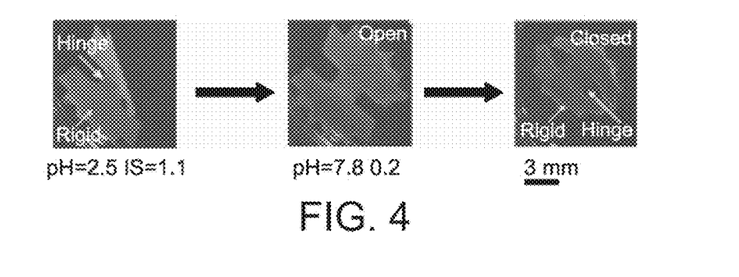
FIG. 4 is a series of pictorial representations of chemically actuated microgrippers that are responsive to pH.

In general, such microgrippers preferably mimic biological appendages, such as claws, with flexible joints between rigid regions. However, those of ordinary skill in the art will appreciate that microgrippers may be any shape that may facilitate grasping of tissue. FIGS. 1A-1H, 2A-2I, 3A-3G and 4 depict various shapes of microgrippers, such as generally star shaped devices (FIGS. 1A-1H, 2A-2I and 3A-3G) and clam shaped devices (FIG. 4).

Microtools or microgrippers for use with the present invention most preferably include a material that is responsive to a magnetic field, such as a magnetic film, coating or solid deposit. Inclusion of a magnetic material in the microgripper allows them to be guided into place with an external magnetic field, and retrieved in turn. Use of a magnetic field allows a metallic microgripper to be magnetically detachable with the device to facilitate removal or deployment of the microgrippers. A variety of different magnets may be utilized. For example, the magnets may be permanent or non-permanent. Exemplary magnets include, rare-earth magnets or magnets including lanthanide elements. Additional magnets include electromagnets which allow control of the magnetic field by the user of the device to enhance manipulation of the microtool.

In one convenient form, the magnetic portion of the microgripper may be comprised of a ferromagnetic material. Non-limiting examples of ferromagnetic materials include Co, Fe, $Fe_2O_3$, $FeOFe_2O_3$, $NiOFe_2O_3$, $CuOFe_2O_3$, $MgOFe_2O_3$, MnBi, Ni, MnSb, $MnOFe_2O_3$, $Y_3Fe_5O_{12}$, $CrO_2$, MnAs, Gd, Dy and EuO. The magnetic material may be incorporated into the microgrippers in any manner that does not inhibit the device from altering conformation to allow grasping of tissue; for example, along rigid, non-articulating portions of the microgripper body.

The microgrippers are bio-inert, and may also be wholly or partially bioresorbable in construction. For example, the microgrippers may be composed completely of bio-inert materials or may be coated with bio-inert materials. As number of materials useful as coatings are well known in the art. Examples of bio-inert coating materials include polymers, such as polyimide, PEEK, polytetrafluorethylene, polyvinylidene fluoride, and polyamide, as well as certain metals, such as gold.

The energy required for the gripping action is intrinsically provided to the microgrippers as a consequence of residual stress stored in the joints and can be released when the hinges are softened (especially if polymeric) or otherwise loosened by heating, delaminated or disintegrated. As a result, the microgrippers require no wires, tethers or batteries to effectuate gripping. The microgrippers may be configured to be responsive to a number of stimuli. In various embodiments, the microgrippers are configured to be responsive to temperature, presence of a chemical, enzymatic degradation, pH, a biomolecules, and the like.

FIGS. 1A-1H, 2A-2I, 3A-3G and 4 show schematic representations of various microgrippers and their operation. FIGS. 1A-1H and 2A-2I show an embodiment of the invention in which the microgrippers are thermo-actuated sub-millimeter microgrippers as disclosed in Leong et al. (*Proc Natl Acad Sci USA* 106:703-8 (2009)). FIGS. 3A-3G shows an embodiment of the invention in which the microgrippers are enzymatically actuated as disclosed in Bassik et al. (*J Am Chem Soc* 132:16314-7 (2010)). FIG. 4 shows an embodiment of the invention in which the microgrippers are chemically actuated by pH.

Microgrippers of the present invention may be of a variety of sizes. In various embodiments, the microgrippers have a major dimension less than about 10, 9, 8, 7, 6, 5, 4, 3, 2 or 1 mm. In an exemplary embodiment, the major dimension is less than about 1, 0.9, 0.8, 0.7, 0.6, 0.5, 0.4, 0.2 or 0.1 mm. Due to their small mm or sub-mm size, hundreds can be dispersed in a small amount of liquid and moved by fluid flow.

As discussed further herein and exemplified in the examples, microgrippers as disclosed herein can retrieve tissue samples, which can then be successfully used for biological analysis, such as histological analysis or evaluation of nucleic acid derived from the samples. For example, as illustrated herein, RNA and DNA extraction may be performed followed by polymerase-chain reaction (PCR) for several genes from tissue retrieved by microtools. Since genetic and epigenetic diagnoses of cancer, inflammatory as well as other mucosal conditions are based on usage of RNA and/or DNA, the biopsy technique of the present invention can produce biologic material that is usable for such analyses.

There are several advantageous features of the microgrippers which allow statistical tissue sampling for applications such as analysis of genetic material contained in the samples. For example, the devices can be fabricated and actuated en-masse in a cost-effective and reliable manner. Also, the devices close in response to a change in local environment, such as body temperature, typically within 5 minutes which enables actuation in a wireless or tetherless manner. Additionally, the devices are relatively bio-inert to provide reduced risk if left behind. Further, the devices are small enough to be deployed with standard surgical catheters. Finally, the devices possess magnetic elements allowing magnetic retrieval and in situ tracking.

A device for deployment and/or retrieval of a tetherless microtool from a subject is also provided by the invention. The device includes one or more magnets configured for retrieval or deployment of a magnetically responsive tetherless microtool. A system for biopsy use including the device comprises both the device, a tetherless microtool magnetically detachable to the one or more magnets and, optionally, a delivery instrument (e.g., an endoscope, laparoscope or other invasive scope).

In particular, one or more magnets constructed as described with respect to the microgrippers are also disposed on or within the microgripper deployment/retrieval device according to the invention. The magnets may be detachably joined to the corresponding magnetically responsive material on the microgrippers.

One of skill in the art would understand that such magnets may be incorporated into the device in a number of ways. For example, magnets may be disposed on or within the device. In various embodiments, a magnet may be integrated into the device during manufacture or disposed on the surface of the device. One of skill in the art would also appreciate that any number and size of magnets may be utilized as well as being incorporated into the device in any pattern that facilitates deployment or retrieval of a microgripper. The magnetic configuration is limited only by the shape of the device.

To provide a surface for carrying the retrieval magnets, the device may further comprise an expandable element, such as an inflatable balloon, resilient coil, stent or spring. If a balloon, the device may be configured as a balloon catheter. In some embodiments thereof, magnets are disposed on the expandable element, and may be integrated therein (e.g., within or as the material forming a coil, stent or spring) or provided thereon as dots or strips (e.g., on the outer surface of a balloon). In some embodiments, the expandable element is disposed at the distal end of the catheter shaft to provide ready contact between the magnets and deployed microtools. Those of ordinary skill in the art will be readily familiar with the myriad of such expandable element devices that are commercially available and suitable for, or adaptable to, use in the invention.

In various embodiments, especially those utilizing a balloon as an expandable element, the device may further include a radiopaque material to allow for detection of the position of the device. A number of radiopaque materials and coatings are well known in the art which may be incorporated onto the surface of the device or otherwise integrated into the device. The radiopaque materials may be incorporated over the entire device or in discrete regions in any number of patterns to allow for detection. In one embodiment, all or part of the expandable element may include radiopaque materials. In some embodiments the distal tip of the device includes radiopaque materials.

Figure 5:
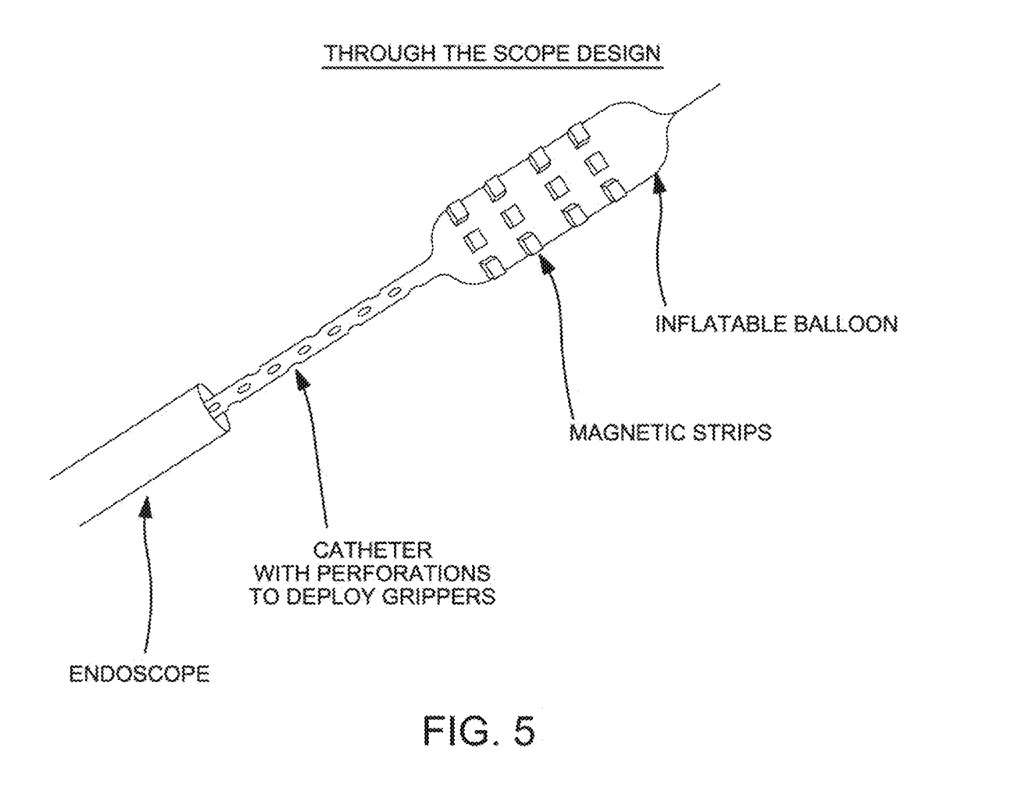
FIG. 5 is a schematic representation of one the device and methodology in one embodiment of the invention.

As noted, the device may conveniently be configured as a catheter sized for passage through the lumen or over the body of an endoscope, laparoscope or other invasive scope device. The catheter may include an elongated shaft of circular cross-sectional shape having proximal and distal ends; and an inflatable balloon disposed on the elongated shaft (FIG. 5). The balloon may be disposed at any point along the catheter shaft. In an exemplary embodiment, the balloon is disposed at the distal end of the shaft. In various embodiments, the balloon includes a wall having proximal and distal portions and having interior and exterior surfaces, the interior surface of the balloon wall being secured to the shaft in a fluid-tight manner. To facilitate inflation of the balloon the shaft may include an inflation lumen in fluid communication with the balloon whereby fluid or gas can be infused and withdrawn to inflate and to deflate the balloon. Fluid or gas may be infused or withdrawn through an accessory port in fluid communication with the inflation lumen which may be adapted to couple with a syringe, external pump, or the like.

Figure 6:
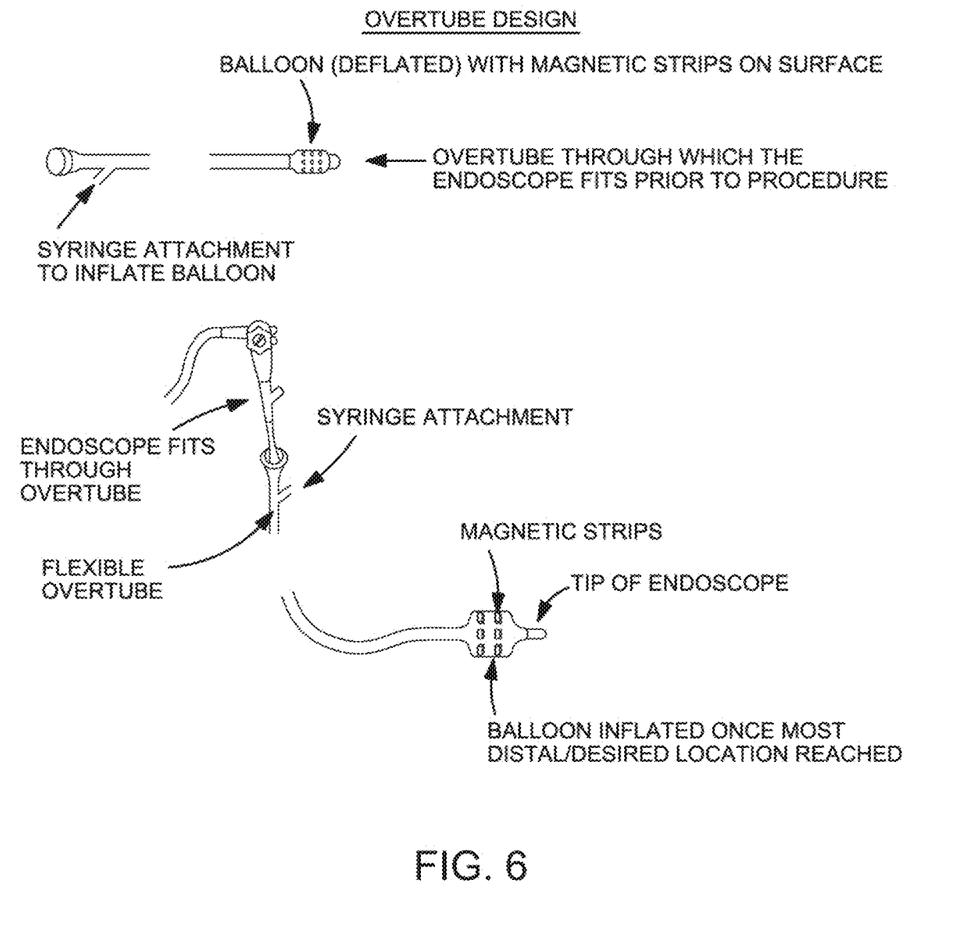
FIG. 6 is a schematic representation of one the device and methodology in one embodiment of the invention.
Figure 7:
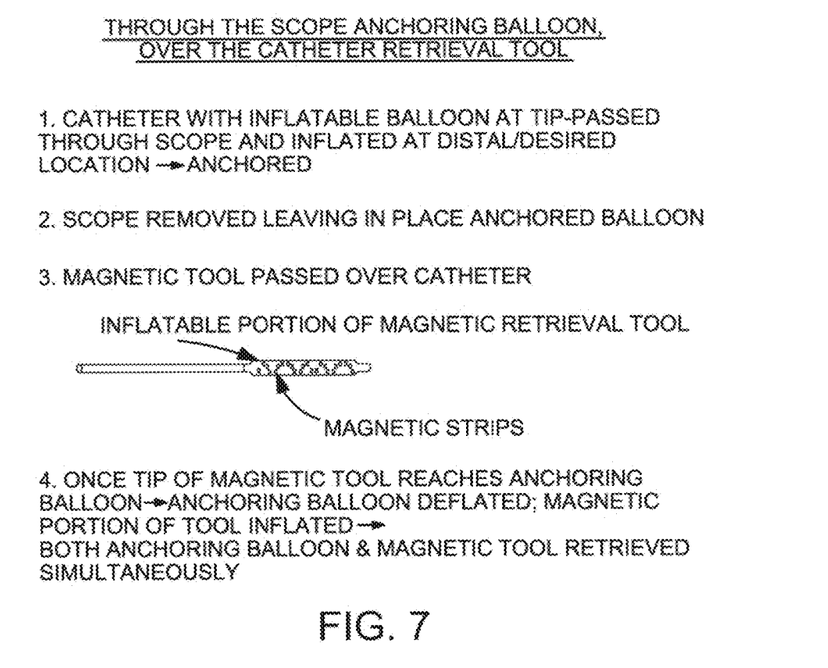
FIG. 7 is a schematic representation of one the device and methodology in one embodiment of the invention.

A shown in FIGS. 5, 6 and 7, the device of the present invention may be configured in a variety of ways to facilitate use of the device with other medical devices. In various embodiments, the device may include a main lumen that extends along the length of the elongated shaft. The lumen may also be sized such that other medical devices may be introduced within the main lumen. For example, an endoscope may be advanced along the main lumen to allow for correct positioning of the device. In various embodiments, the elongated shaft of the device may be flexible or rigid.

With reference to FIG. 5, a particularly preferred deployment/retrieval device for use in the methods of the invention is configured as a catheter having an inflation balloon disposed at the distal end of the device. The device is configured such that it may be advanced though the lumen of an endoscope or overtube into a cavity of a subject. The device may include one or more opening in the elongated shaft to allow for deployment of the microgrippers. In the embodiment depicted in FIG. 5, a plurality of openings are disposed proximal to the balloon. However, in other embodiments, the openings may be disposed at any point along the shaft of the device, for example, openings may be disposed through the balloon region or distal to the balloon.

In various embodiments, the microgrippers are deployed through a catheter through openings which may be disposed in any number of configurations. The microgrippers are typically suspending in a small volume of fluid in a syringe, such as water. The syringe may then be attached to the catheter and the microdevices injected.

As shown in FIG. 5, the distal inflation balloon includes magnets disposed in a radially circumferential pattern around the balloon. One of skill in the art would understand that the magnets may be disposed in other pattern to achieve similar functioning of the device, such as being disposed as longitudinal stripes or being disposed over the entire distal end or balloon of the device. In various embodiments, the magnets may be flexible or rigid.

With reference to FIG. 6, in one embodiment, the present invention provides a device configured as an overtube having an inflation balloon disposed at the distal end of the device. The device is configured such that it allows advancement of a second device along a lumen of the device. For example, an endoscope or catheter may be advanced along the lumen of the device facilitate placement of the device with the a tissue cavity of a subject. In one embodiment, an endoscope or catheter is advanced along the lumen of the device before the device is place within the tissue cavity. The device is then advanced along the tissue cavity to a desired location at which point the device may be anchored by inflating the distal balloon.

One skilled in the art would understand that the device may include any number of balloons or other expandable elements disposed along the elongated shaft. For example, 1, 2, 3, 4 or more balloons or other elements may be disposed along the shaft.

For clinical use, the present invention provides a method of tissue sampling. The method includes: a) contacting a plurality of tetherless microtools with a tissue of a subject, each microtool having a first configuration; b) allowing the plurality of tetherless microtools to alter from the first configuration to a second configuration while in contact with the tissue, the second configuration adapted such that each microtool grasps the tissue at a discrete location; c) retrieving the plurality of tetherless microtools from the subject using a device comprising one or more magnets, wherein each microtool retains an individual sample of the tissue upon retrieval, thereby performing tissue sampling. In various embodiments, the tetherless microtools are deployed and/or retrieved from the subject using the device of the present invention.

For example, where the retrieval device of the invention is a catheter having an inflation balloon disposed at its distal end, the catheter may be advanced along a tissue cavity along with an endoscope disposed in the lumen of the catheter. Upon reaching a desired location, the catheter may be anchored by inflating the balloon. The endoscope is then removed.

Microgrippers may be deployed through the catheter or otherwise before or after anchoring of the catheter. The device of the invention having an elongated shaft including a distal balloon and main lumen extending along the length of the shaft is then passed over the anchored catheter. Once the distal tip of the device reaches the anchoring balloon of the catheter, the anchoring balloon is deflated and the balloon of the device is inflated. Magnets disposed in the balloon of the device contact microgrippers within the body cavity. The device and catheter are then removed simultaneously from the body cavity.

Any number of microgrippers may be deployed within a body cavity. In various embodiments, 1 to 10, 1 to 50, 1 to 100, 1 to 250, 1 to 500, 1 to 1000 or greater microgrippers are deployed and retrieved from a body cavity. As such, one of skill in the art would understand that varying amounts of tissue may be retrieved from the cavity which may be utilized for analysis.

The device and methodology of the invention allow for randomized statistical sampling of tissue. As such, in one aspect, the invention provides a method of obtaining a randomized statistical tissue sample during a diagnostic biopsy of a subject. The method includes a) introducing a plurality of tetherless microtools into a cavity of a subject; b) introducing a device comprising an expandable element having one or more magnets into the cavity; c) anchoring the device via the expandable element so as to facilitate contact between the expandable element and the plurality of tetherless microtools; d) withdrawing the device so that the plurality of tetherless microtools collect on the expandable element via magnetism and are removed from the subject, wherein each of the plurality of tetherless microtools comprise an individual tissue sample from the cavity; and e) processing the samples for diagnostic biopsy.

As used herein, the term "sample" refers to any biological material retrieved from a subject by a microgripper. For example, a sample can be any sample that includes a cell or other biological material that may be utilized for further analysis, including, for example, a tissue, a bodily fluid, or a sample of an organ.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The methodology and device of the present invention may be deployed to biopsy or obtain a sample of any area of the body. Generally, microgrippers are deployed to a body cavity, such as a hollow organ of the body, for example the gastrointestinal tract. However, microgrippers may be deployed to any area of the body to obtain a sample. As such, the term "body cavity" is intended to refer to internal surfaces and spaces of the body, as well as external surfaces of the body. In exemplary embodiments, a sample is obtained from a mucosal or epithelial cell lined surface, such as the pulmonary or respiratory tract, or gastrointestinal tract. In other exemplary embodiments, a sample is obtained from a duct or gland, such as a bile duct. In other exemplary embodiments, a sample is obtained from an organ or tissue.

In various embodiments, the method of the invention further includes analyzing the individual samples retrieved by the microtools. One of skill in the art would appreciate that any number of analysis may be performed using the samples to facilitate diagnosis or prognosis of a condition or disorder.

Accordingly, in another aspect, the present invention provides a method of diagnosing a condition or disease in a subject. The method includes: a) obtaining a tissue sample from a subject via the method of the invention; b) analyzing the tissue sample; and c) providing a diagnosis of the condition or disease based on the analysis.

In another aspect, the present invention provides a method of providing a prognosis for a condition or disease in a subject. The method includes: a) obtaining a tissue sample from a subject via the method of the invention; b) analyzing the tissue sample; and c) providing a prognosis of the condition or disease based on the analysis.

As such, the method of the present invention may be used, for example, to evaluate cancer patients and those at risk for cancer. In any of the methods of diagnosis or prognosis described herein, either the presence or the absence of one or more indicators of cancer, such as, a cancer cell, or of any other disorder, may be used to generate a diagnosis or prognosis.

Samples obtained from a subject may be used to investigate and identify any number of conditions or disorders. As used herein, the terms "condition," "disease," or "disorder" are used to refer to a variety of pathologies. For example, the term may include, but is not limited to, various cancers, immune pathologies, neurodegenerative diseases, and the like. The term "cancer" as used herein, includes a variety of cancer types which are well known in the art, including but not limited to, dysplasias, hyperplasias, solid tumors and hematopoietic cancers. Additional cancers may include, but are not limited to, the following organs or systems: brain, cardiac, lung, gastrointestinal, genitourinary tract, liver, bone, nervous system, gynecological, hematologic, skin, breast, and adrenal glands. Additional types of cancer cells include gliomas (Schwannoma, glioblastoma, astrocytoma), neuroblastoma, pheochromocytoma, paraganlioma, meningioma, adrenalcortical carcinoma, medulloblastoma, rhabdomyoscarcoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia; and skin cancers including malignant melanoma, basal cell carcinoma, squamous cell carcinoma, Karposi's sarcoma, moles dysplastic nevi, lipoma, angioma, dermatofibroma, keloids, sarcomas such as fibrosarcoma or hemangiosarcoma, and melanoma.

Once obtained, a sample is typically further processed and analyzed. Processing of the sample may include isolation of a biological component of the sample, such as a protein, a nucleic acid molecule, or individual cell. In some embodiments, the sample is processed to isolate nucleic acids, such as DNA and RNA. In some embodiments, the sample is processed to isolate individual cells.

The term "nucleic acid molecule" is used broadly herein to mean a sequence of deoxyribonucleotides or ribonucleotides that are linked together by a phosphodiester bond. As such, the term "nucleic acid molecule" is meant to include DNA and RNA, which can be single stranded or double stranded, as well as DNA/RNA hybrids. Furthermore, the term "nucleic acid molecule" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR), and, in various embodiments, can contain nucleotide analogs or a backbone bond other than a phosphodiester bond.

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Of course, it will be recognized that an "oligonucleotide" also can encode a peptide. As such, the different terms are used primarily for convenience of discussion.

In various embodiments, a sample may be analyzed in a variety of ways to identify a condition or disorder. Typically, the analysis include investigation of one or more nucleic acid molecules to diagnose a disease or condition, e.g., genetic analysis. In some embodiments, a sample may be analyzed by performing image analysis of individual cells to, for example, characterize cell type and cell morphology. Detectable markers, such as cell surface markers and nuclear markers, cell type, cell size, cell shape and the like may be analyzed using various microscopy and imaging techniques known in the art.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule.

Any number of analyses may also be performed of the sample or component thereof, to provide clinical assessment. For example, gene expression analysis and PCR techniques may be employed, such as gene chip analysis and multiplexing with primers specific for particular markers to obtain information such as the type of a tumor, metastatic state, and degree of malignancy. In some embodiments, expression of individual genes associated with a disease or disorder is examined. In some embodiments, expression of cell surface markers may be analyzed. As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker.

Additionally, cell size, DNA or RNA analysis, proteome analysis, or metabolome analysis may be performed as a means of assessing additional information regarding characterization of a disease or disorder. In various aspects, analysis may include antibodies directed to or PCR multiplexing using primers specific for one or more of markers. Examples of well known cancer markers include: EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, and Leukocyte Associated Receptor (LAR).

Analysis may also include performing methylome analysis or detecting the methylation status of an isolated nucleic acid molecule. In various embodiments, the determining of methylation status is performed by one or more techniques selected from a nucleic acid amplification, polymerase chain reaction (PCR), methylation specific PCR, bisulfite pyrosequenceing, single-strand conformation polymorphism (SSCP) analysis, restriction analysis, microarray technology, and proteomics. Analysis of methylation can be performed by bisulfite genomic sequencing. Bisulfite treatment modifies DNA converting unmethylated, but not methylated, cytosines to uracil. Bisulfite treatment can be carried out using the METHYLEASY™ bisulfite modification kit (Human Genetic Signatures). Other methods are known in the art for determining methylation status, including, array-based methylation analysis, Southern blot analysis, molecular beacon technology, Taqman™ technology, methyl light, Methyl Heavy, or SNuPE (single nucleotide primer extension). The degree of methylation in a nucleic acid molecule may also be measured by fluorescent in situ hybridization (FISH).

With regard to cancer, analysis allows for meaningful characterization useful in assessing diseases prognosis and in monitoring therapeutic efficacy for early detection of treatment failure that may lead to disease relapse. In addition, analysis enables the detection of early relapse in presymptomatic patients who have completed a course of therapy. Thus, enumeration and characterization of specific cells of a sample provides methods to stratify patients for baseline characteristics that predict initial risk and subsequent risk based upon response to therapy.

In various aspects, samples may be obtained and analyzed over a particular time course in various intervals to assess a subject's progression and pathology. For example, analysis may be performed at regular intervals such as one day, two days, three days, one week, two weeks, one month, two months, three months, six months, or one year.

Analysis may provide data sufficient to make determinations of responsiveness of a subject to a particular therapeutic regime, or for determining the effectiveness of a candidate agent in the treatment of a disease or disorder, such as cancer. For example, once a drug treatment is administered to a patient, it is possible to determine the efficacy of the drug treatment using the method of the invention. For example, a sample taken from the patient before the drug treatment, as well as one or more cellular samples taken from the patient concurrently with or subsequent to the drug treatment, may be isolated and processed using the method of the invention. By comparing the results of the analysis of each processed sample, one may determine the efficacy of the drug treatment or the responsiveness of the patient to the agent. In this manner, early identification may be made of failed compounds or early validation may be made of promising compounds.

Analysis of a sample during a clinical trial will provide information on whether the patient is responding or not responding to an experimental drug. This information is an early indicator of the drug's effectiveness and may be used by the investigators as a secondary endpoint in the clinical trial.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Tissue Sampling of Pig Colon

In a significant step towards enabling non-invasive surgery, this example describes sampling of gastrointestinal tissue using sub-millimeter sized tetherless microtools, in the form of microgrippers. The microgrippers were fabricated using conventional multilayer microfabrication and were composed of rigid segments connected to pre-stressed metallic bilayer hinges covered by a thermo-sensitive polymer trigger. On exposure to body temperature, the open microgrippers close spontaneously, typically within five minutes. This example shows ex-vivo proof-of-concept tissue sampling by deploying the microgrippers through a catheter. Subsequent retrieval of the grippers with a magnetic probe enabled tissue acquisition for viable molecular diagnostics. Microgrippers were used to retrieve tissue endoscopically, from which RNA and DNA were extracted. Polymerase-chain reaction (PCR) was also performed for several genes on the extracted genetic material.

Microgrippers were modeled as biological appendages, such as claws, by designing flexible joints between rigid regions, as described in Leong et al. (*Proc Natl Acad Sci USA* 106:703-8 (2009)). Due to their small sub-mm size (~0.98 mm from tip to tip when completely open), it was possible to deploy hundreds of them. The rigid regions of the grippers are composed mostly of nickel, a ferromagnetic material, so that the grippers can be guided with an external magnetic field from afar. Also, the nickel parts were covered by gold to render them bio-inert. FIGS. 1A-1H show the schematic representation of the grippers and their operation used in this example.

The following experimental methods and protocols were utilized.

Microgrippers. The microgrippers were fabricated on silicon substrates utilizing standard photolithography techniques and released from the substrate prior to the endoscopic experiments as described in Leong et al. (*Proc Natl Acad Sci USA* 106:703-8 (2009)). After the grippers were released from the substrate, they were rinsed several times in DI water and kept at ~0° C. till their deployment to the colon.

Animal Tissue. Pig colons were obtained from a local slaughterhouse minutes after the animals were butchered. The pig colons were immediately placed and kept on ice until the next day when the endoscopic experiments were performed. The resection piece included an intact colon, from anus to cecum. To facilitate endoscopic visual inspection of the pig colon, the colon was tied at the cecum with a plastic band, so that air insufflation would result in distension of the colon and adequate mucosal inspection.

Endoscopic Equipment. For the endoscopic experiments a standard Pentax™ EG-3840T double channel (therapeutic) endoscope was used. A single channel endoscope can also be used in a similar fashion with the exception that the catheter used to deploy the grippers needs to be removed prior to re-using the same port for the magnetic catheter to retrieve the microgrippers.

Microgripper Retrieval and Analysis. A grade N52, Neodymium magnet (K&J Magnetics Inc, Jamison, Pa.) was used to build a magnetic catheter for endoscopic retrieval of grippers. A group of retrieved grippers were stained with trypan blue (Sigma-Aldrich, St. Louis, Mo.) to image the cellular media under the optical microscope. Another group of grippers were quickly submerged in Trizol (for RNA extraction) or Viagen solution (for DNA extraction) immediately after the retrieval.

DNA and RNA Extraction. The RNA was extracted by using TRIzol™ reagent (Invitrogen, Carlsbad, Calif.). RNA specimens were stored at −80° C. prior to analysis. Reverse transcription was performed by using the kit from Fermentas (Catalog number K1612) (Fermentas Inc, Glen Burnie, Md.). DNA was extracted with the Viagen solution (Catalog number 102-T) (Viagen Biotech, Los Angeles, Calif.), by following the manufacturer's protocol.

Results

Figure 8A:
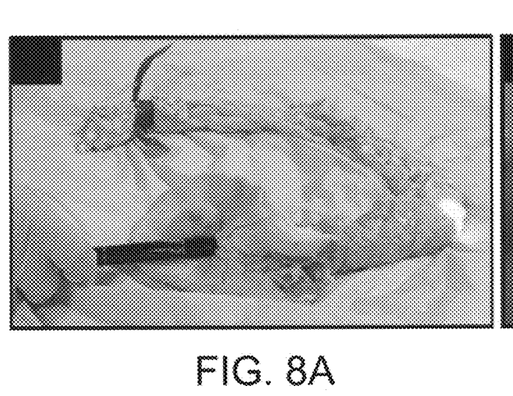
FIG. 8A is an optical image of colon preparation for endoscopic visualization.
Figure 8B:
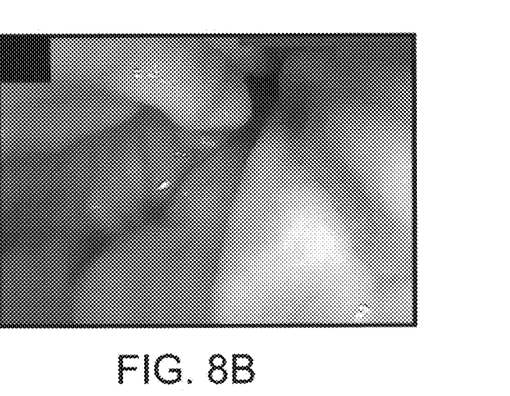
FIG. 8B is an endoscopic image of porcine colon.

Swine Model for Ex-vivo Colonoscopy. To evaluate the feasibility of statistical tissue sampling from hollow gastrointestinal organs using microgrippers, ex-vivo colonoscopies were performed on pig colon, which was chosen because of its similarities to human colon in terms of size and endoscopic appearance. A human therapeutic (double channel) upper endoscope was used for these experiments. The endoscope was inserted through the anus and advanced under endoscopic guidance to the cecum and then withdrawn while the mucosa was inspected (FIG. 8A). Except for mucosal pallor, which was expected given the lack of blood supply, the colonic mucosa appeared remarkably similar to human colonic mucosa (FIG. 8B).

Endoscopic Deployment and Intraluminal Activation of the Microgrippers. The hinge layer of the microgrippers is thermo-sensitive and when exposed to the transition temperature, (37° C.), the hinges bend and the microgrippers close. After being subjected to this temperature, it takes about 5 minutes for the grippers to completely close and grip proximal tissue. Prior to the procedure, the open grippers were kept in cold water (~0° C.) to prevent premature closing. To mimic the normal human body temperature, the colon was placed in a water bath kept at 37° C. A catheter was inserted through one of the channels of the endoscope.

Figure 9A:
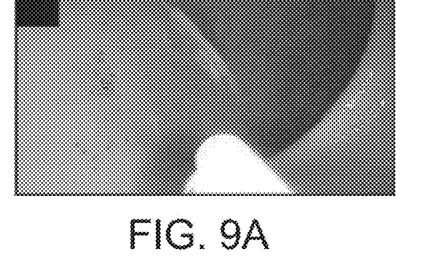
FIG. 9A is an image showing microgrippers deployed in one area in the colon.
Figure 9B:
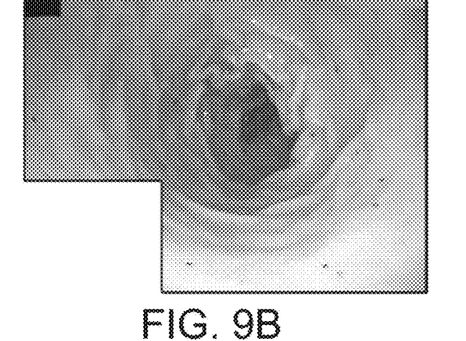
FIG. 9B is an image showing microgrippers covering the colon surface, in a different deployment.

In the first set of experiments, approximately 30 microgrippers suspended in sterile water were aspirated into the catheter and then deployed on an area approximately 4 cm$^2$ in size. FIG. 9A shows an endoscopic image of the deployed grippers on colonic mucosa. The number of deployed microgrippers was varied later to test for the ability to spread the grippers for a wide sampling of the colonic mucosa. A uniform spread of the microgrippers was achieved when the endoscope was continuously whirled during the deployment of large number of grippers (approximately 100) as seen in FIG. 9B. The number of deployed grippers is important to improve the statistical efficacy of sampling.

Figure 9C:
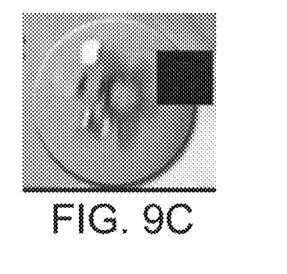
FIG. 9C is a close up image of microgrippers closing on the colon wall.

When grippers were deployed in the colon, soon after mucosal contact, they were activated by the colonic temperature (37° C.) and closed. The closure of the grippers was verified endoscopically. Most grippers closed onto the colonic mucosa (FIG. 9C) while very few grippers closed towards the colon cavity.

Figure 9D:
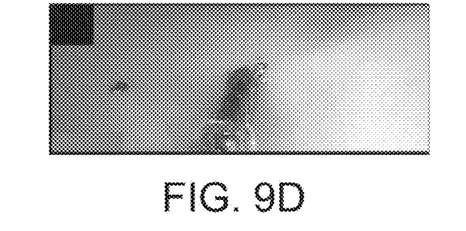
FIG. 9D is an image showing magnetic retrieval of the microgrippers.

Magnetic Retrieval of the Grippers. A specially designed catheter featuring a magnetic tip was used to retrieve the microgrippers. The catheter was inserted through the second channel of the endoscope and used to collect the grippers; FIG. 9D shows the retrieval of the grippers by magnetic catheter. The vast majority of grippers were successfully captured with the magnetic catheter and the rest were successfully suctioned with the endoscope into a trap bottle.

Figure 10A:
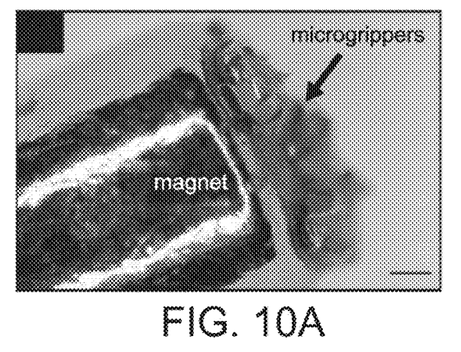
FIG. 10A is an image showing retrieved grippers on a magnetic retrieval device configured as a catheter in one embodiment of the invention.
Figure 10B:
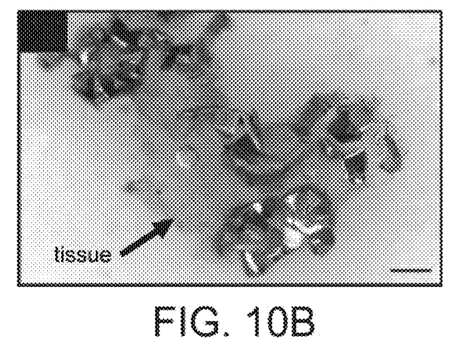
FIG. 10B is an image showing the retrieved tissue after staining with trypan blue. Scale bars represent 200 µm.

A group of retrieved grippers were imaged with optical microscopy to verify that they obtained tissue from the colonic mucosa, FIG. 10A. Next, the grippers and associated tissue were separated from the magnetic tip and stained with trypan blue, a tissue stain. FIG. 10B shows that the blue stained cellular material is attached to the grippers confirming that the retrieved grippers returned with cellular material.

Figure 10C:
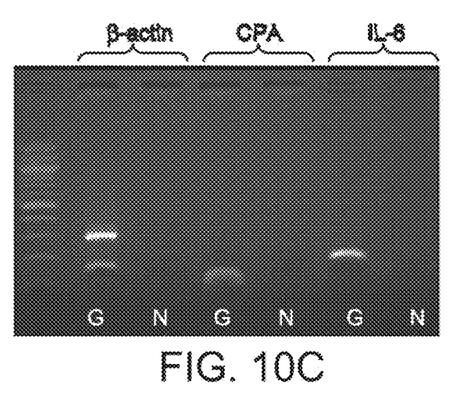
FIG. 10C is an image of an electrophoresis gel of PCR of cDNA from the tissue obtained with microgrippers (G) compared to negative control (N).
Figure 10D:
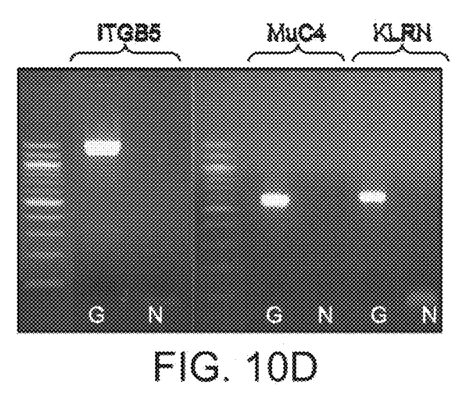
FIG. 10D is an image of an electrophoresis gel of PCR of genomic DNA from tissue retrieved by grippers.

Genetic Analyses of RNA and DNA of the Tissue Obtained Through the Grippers. A second group of retrieved grippers was used to extract RNA and DNA from the obtained tissue. The concentration of RNA was measured, on average 122 ng/pt and the concentration of DNA was measured, on average, 134 ng/μL. The RNA was reverse transcribed, and the complementary DNA (cDNA) was utilized as template for PCR. Primers designed for pig Beta-actin, Cyclophilin-A (CPA) and Interleukin-6 (IL-6) were employed, because of the relative high abundance of these transcripts. As FIG. 10c demonstrates, cDNA amplification produced bands of expected size. Similarly, DNA primers designed for pig DNA Kalirin (KALRN), Mucin 4 (MUC4) and Integrin beta 5 (ITGB5) were employed, due to the relative high abundance of these genes. Subsequently, standard PCR followed by gel electrophoresis were performed. FIG. 10D demonstrates that all 3 genes tested were successfully amplified and that the amplified DNA had the expected size.

In cases where the macroscopic appearance of the mucosa is unrevealing, random biopsies are required. In these cases, broad mucosal coverage is desired. In addition, making a diagnosis of a premalignant or malignant condition is oftentimes more important than the precise location of the abnormality. Examples include diagnosing dysplasia in ulcerative colitis, microscopic/collagenous colitis or *Helicobacter Pylori* infection. This example describes an innovative endoscopic biopsying technique that employs tetherless microgrippers. These microgrippers can be deployed, activated and retrieved endoscopically, as demonstrated by the experiments on pig colon.

The device and methodology of the present invention differs significantly from the traditional biopsy forceps. Due to miniaturized size of the microgrippers and their deployment method, e.g., spraying the grippers through the catheter, it is possible to achieve expansive randomized biopsy sites and consequently better mucosal coverage. In addition, the microgrippers, due to their minute size, likely result in less mucosal damage than the traditional biopsying forceps potentially resulting in fewer endoscopic side effects.

Due to the sub-millimeter size of the grippers, the amount of tissue retrieved by each gripper is significantly less than the tissue obtained by traditional biopsy forceps. However, the amount of tissue gathered by traditional forceps from each biopsy sites may be unnecessary for genetic or epigenetic diagnoses. As show in this example, the tissue retrieved by the grippers is of sufficient quality and quantity to allow DNA as well as RNA extraction.

In an era of major molecular biology advances on genome sequencing as well as on mRNA, miRNA and epigenetic studies, an ever increasing number of gene alterations can be identified. These alterations, either individually, or in combination, can be utilized to diagnose diseases. When several mucosal conditions are not readily detectable by traditional endoscopic inspection, a protocol of randomized biopsy is necessary. In these cases, the best mucosal coverage obtained with minimal damage to the rest of the mucosa is highly preferred. This example demonstrated the feasibility of using tetherless thermo-actuated microgrippers for the randomized endoscopic tissue sampling.

Example 2

In-Vivo Bile Duct Tissue Sampling Through Endoscopic Retrograde Cholangiopancreatography (ERCP)

This example describes sampling of bile duct tissue through ERCP.

The microgrippers were fabricated on silicon substrates utilizing standard photolithography techniques and released from the substrate prior to the endoscopic experiments as described in Leong et al. (*Proc Natl Acad Sci USA* 106:703-8 (2009)) and discussed in Example 1.

Figure 11:
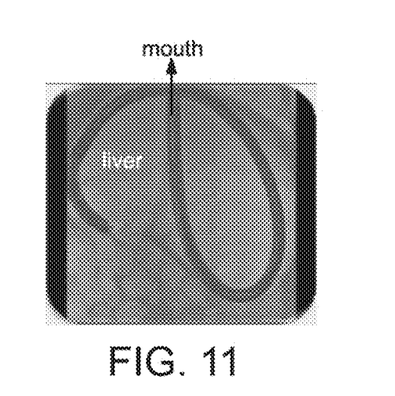
FIG. 11 is a pictorial representation showing catheter insertion in bile duct tissue sampling.
Figure 12A:
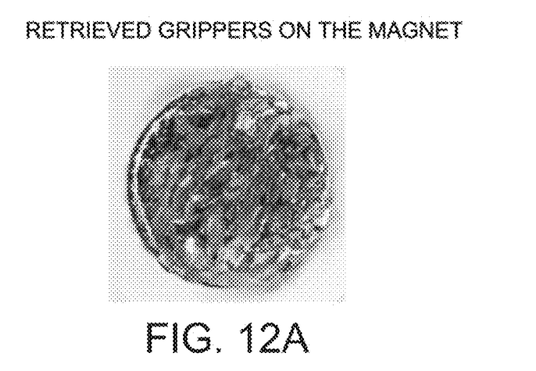
FIG. 12A is an image showing retrieved grippers on a magnetic retrieval device configured as a catheter in one embodiment of the invention.
Figure 12B:
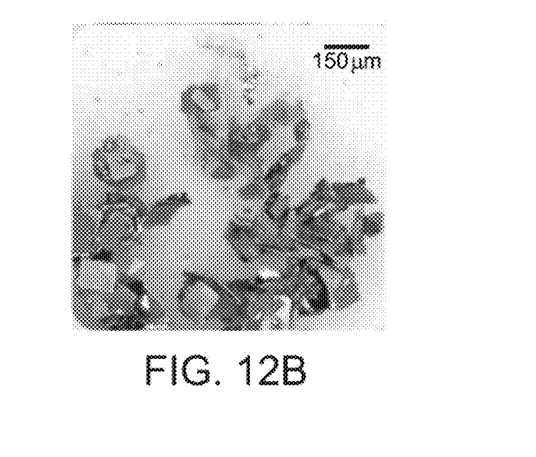
FIG. 12B is an image showing the retrieved tissue after staining with trypan blue. Scale bars represent 150 µm.

Microgrippers were deployed into the bile duct through an ERCP catheter and retrieved via a device of the present invention configured as a magnetic catheter. FIG. 11 shows introduction of the catheter. FIG. 12A shows retrieved microgrippers on the magnet of the catheter as well as retrieved microgrippers detached from the magnet and stained with trypan blue.

After removal of the microgrippers, the liver of the pig was removed to assess the retrieval rate of microgrippers. The liver was image though magnetic resonance. Only 2 grippers were found to remain in the liver, whereas more than 40 were successfully retrieved. As such the retrieval rate observed was greater than 95%.

Example 3

Enzymatically Actuated Microgrippers

This example describes sampling using enzymatically actuated microdevices.

Multilayer grippers with hinges composed of either gelatin, a polypeptide, or carboxymethylcellulose (CMC), a polysaccharide were generated as disclosed in Bassik et al. (*J Am Chem Soc* 132:16314-7 (2010)). These hinges contained pre-stressed and structural metal films, were patterned using photolithography and combined with rigid segments to create a gripper. These tools closed and re-opened when exposed to proteases and glucosidases respectively. They were approximately 1.1 mm in diameter when open and approximately 600 μm in diameter when closed (FIGS. 13A-13I). The fabrication process was highly parallel and approximately 1600 grippers could be fabricated simultaneously on a three inch diameter wafer.

Figures 13A, 13D:
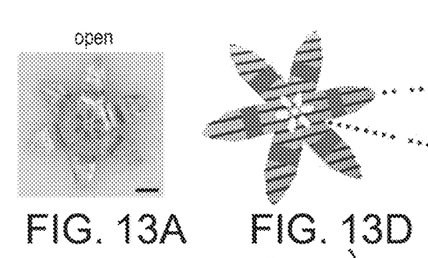
Figure 13B:
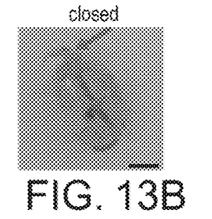
Figure 13C:
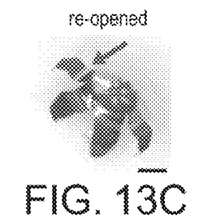
Figure 13E:
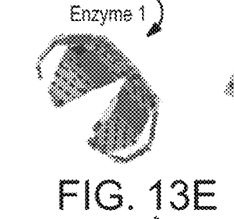
Figure 13F:
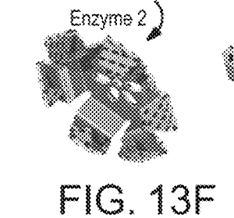
Figure 13G:
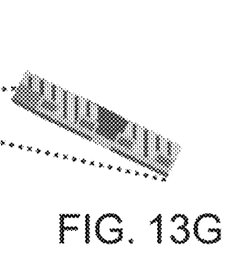
Figure 13H:
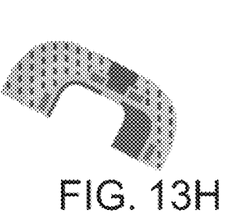
Figure 13I:
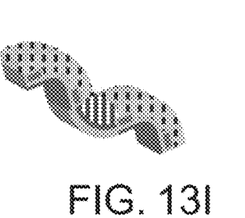

Grippers were designed with alternating rigid segments and flexible hinges. Rigid segments remained flat during the entire cycle of closing and re-opening, providing the mechanical strength required for secure gripping. Flexible hinges were initially flat, and curved only on exposure to the appropriate enzyme. Closing and re-opening was achieved using a gripper design with two kinds of hinges which bent with either concave or convex curvatures. The concept behind this two-stage actuation is as follows: on the appropriate trigger, all hinges covered with one biopolymer actuate, while the entire second set of hinges remain flat, causing the gripper to close. As the modulus of the second biopolymer is reduced, all the second hinges also bend, but in the opposite direction, thus re-opening the gripper (FIG. 13B).

The grippers were microfabricated in two dimensions (2D) on a silicon wafer using conventional photolithography techniques and were subsequently released from the substrate. The first step involved depositing a sacrificial copper (Cu) layer on the wafer by thermal evaporation. Next, flexible and rigid components consisting of chromium (Cr), nickel (Ni) and gold (Au) were deposited and patterned by lift-off metallization and electrodeposition. Ni, which is ferromagnetic, was incorporated to allow for remote magnetic manipulation. The gripper was designed such that only Cr and Au surfaces were exposed to render it bio-inert. Aqueous biopolymer solutions were dispensed onto the features and patterned by exposure to ultraviolet (UV) light through a quartz photomask. The uncrosslinked biopolymer was washed away, and the sacrificial layer was dissolved to release untethered grippers.

Commercially processed derivatives were chosen of natural biopolymers to allow for aqueous handling: gelatin, derived from collagen, and CMC, from cellulose. The two biopolymers are targeted by different families of enzymes—without overlapping activity—so that each set can be actuated selectively. Additionally, it is known that gelatin is degraded by enzymes which occur in disease states, such as proteases in cancer. This offers the possibility for autonomous actuation in response to a disease marker. The other biopolymer, CMC, degrades on exposure to non-mammalian enzymes that do not interact with animal tissue.

Both raw biopolymers were synthetically modified by chemical grafting of methacrylate groups to the polymer backbone. This modification enabled cross linking under UV light in the presence of molecular crosslinkers and free-radical photoinitiators. The highlight of this process is that the crosslinked material retained the necessary accessible monomer groups to allow for enzymatic recognition and cleavage.

Figure 14:
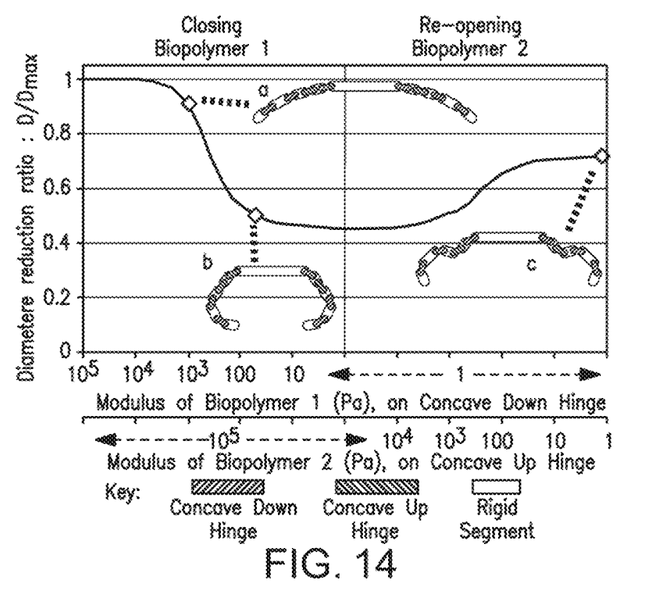
FIG. 14 is a graphical representation depicting mathematical modeling of the actuation of microgrippers (of FIGS. 13A-13I) as a function of moduli of biopolymers. Letter (a) of the Figure indicates that in the initial state both polymers are stiff (moduli higher than $10^4$ Pa) and the entire gripper is flat. Letter (b) of the Figure indicates that when the first biopolymer is degraded and its modulus decreased to approximately 100 Pa, the first set of six hinges bends causing the gripper to close. Letter (c) of the Figure indices that the remaining two hinges bend when the modulus of the second biopolymer trigger is decreased.

The biopolymers were patterned sequentially atop the metal layers, while underlying multilayer hinges were constructed by layering thin films with specific levels of tension. The bending angles of the hinges were designed using a multilayer mechanics model. The magnitude of the strain differential across the thickness of this multilayer stack leads to a specific bending angle at equilibrium. Controlled bending of the multilayer hinge was achieved by altering the mechanical properties of the biopolymer. A relatively stiff crosslinked biopolymer on top of a pre-stressed bilayer stack arrested its bending, causing it to remain flat. Removal or softening of this biopolymer allowed the hinge to bend (FIG. 14).

Using the model, it was determined that for a typical gel modulus of $10^4$ Pa, a 150 μm thick patterned gel would be sufficient to ensure a flat state, which was verified experimentally. In order to create a miniaturized integrated tool we used a computer simulation to model serial linkages of rigid segments and various hinge types as a 2D cross section, so that the folding state of any tool could be visualized in silico before experiments. Grippers were first simulated with a single set of hinges that simply closed on actuation. Using this model, it was observed that a reduction in modulus to 100 Pa would cause the gripper to close, and observed a similar actuation profile in experiments (FIG. 2G).

Grippers were then modeled with two sets of hinges that closed and re-opened. Closing occurred when the modulus of the first biopolymer (CMC) was reduced to 100 Pa while the second biopolymer (gelatin) remained stiff ($10^4$ Pa) (FIG. 14). Re-opening occurred when the modulus of gelatin was reduced in turn. During the actuation of the gelatin-triggered hinge, the modulus of CMC remained low and was not affected.

Selectivity of actuation was studied using grippers with either a gelatin or a CMC trigger. Several enzymes were screened including proteases from animal pancreatic origin (trypsin), plant origin (papain), and bacterial origin (collagenase), which are specific to the polypeptide (gelatin) grippers, and carbohydrate degrading enzymes from fungal origin (cellulase) that are specific to the polysaccharide (CMC) trigger. A commercial mixture of many carbohydrases used for plant cell wall lysis (Viscozyme) were tested, as well as phosphate buffered saline (PBS) and cell culture media with serum. For these experiments, special care was taken to ensure that all grippers were fabricated simultaneously on a single wafer and differed only in the application of gelatin or CMC hinge triggers as a final step.

Figure 1A:
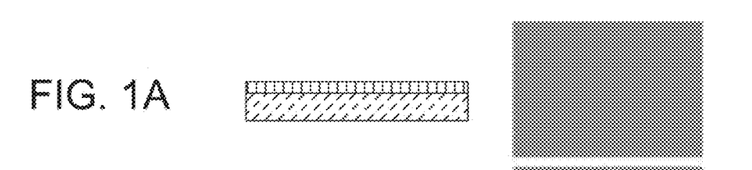
FIG. 1A shows use of a thin Cu layer as the sacrificial layer.
Figure 1B:
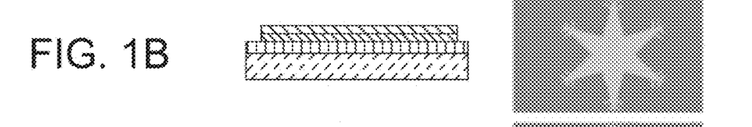
FIG. 1B shows a pre-stressed Cr—Au bilayer patterned and evaporated.
Figures 1C, 1D:
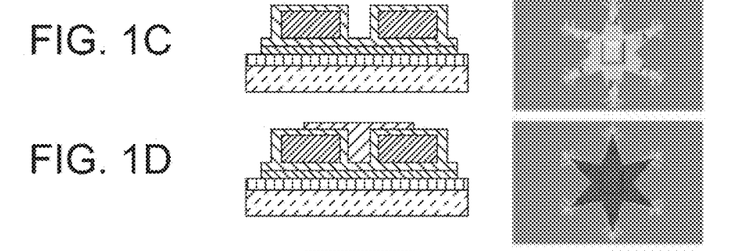
FIG. 1C shows electroplating of ferromagnetic Ni as the rigid segments between the hinges and covered with Au.
FIG. 1D shows patterning of thermo-sensitive polymeric trigger.
Figure 1E:
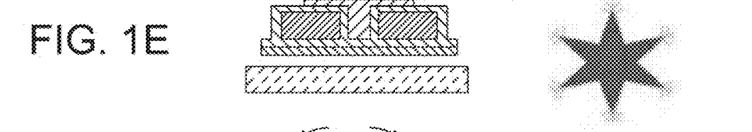
FIG. 1E depicts lifting-off the microgrippers from the substrate by dissolving the sacrificial layer.
Figure 1F:
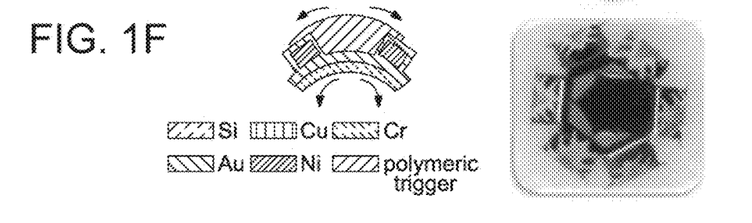
FIG. 1F depicts closed microgrippers (conformational change to a second structural conformation) when exposed to transition temperature.
Figure 1G:
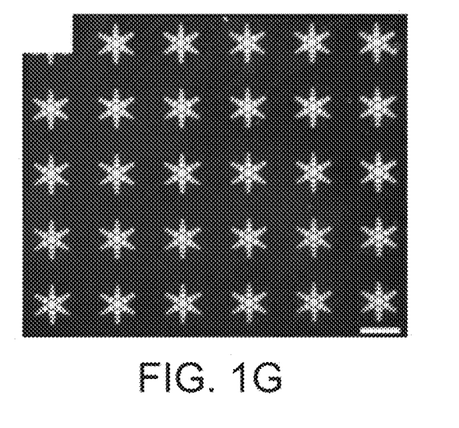
FIG. 1G depicts optical microscopy imaging of the microgrippers on the Si substrate before the lift-off process.
Figure 1H:
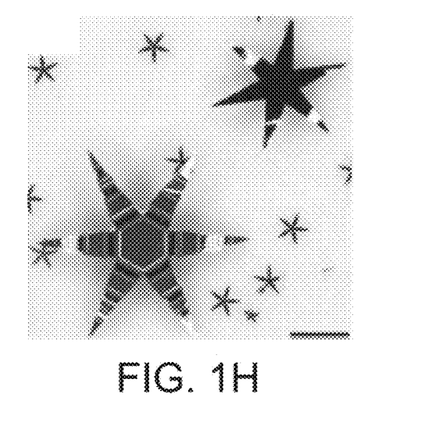
FIG. 1H depicts optical microscopy images of different size microgrippers after the lift off. The scale bars represent 400 µm.
Figure 2A:
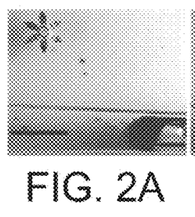
Figure 2B:
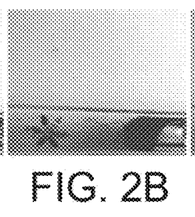
Figure 2C:
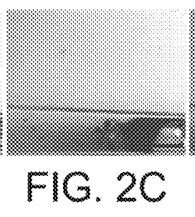
Figure 2D:
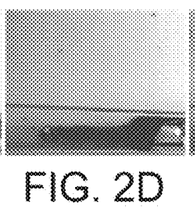
Figure 2E:
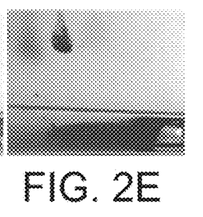
Figure 2F:
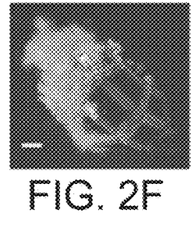
FIG. 2F and FIG. 2G are images showing microgrippers capturing cells. The scale bars are 100 µm.
Figure 2G:
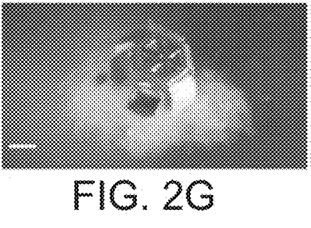
Figure 2H:
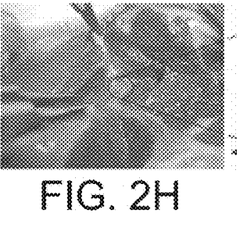
FIGS. 2H and 2I are images of an ex-vivo biopsy procedure showing microgrippers in one embodiment of the invention is the intrahepatic bile ducts. The scale bar is 1 mm.
Figure 2I:
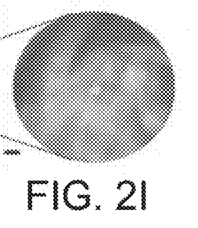
Figure 3A:
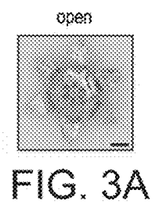
FIGS. 3A-3C provide images of microgrippers patterned with bio-polymers in one embodiment of the invention.
Figure 3B:
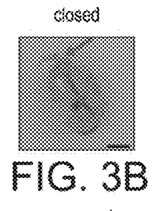
Figure 3C:
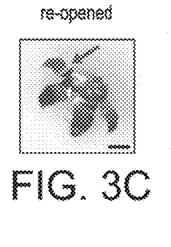
Figures 3D, 3E, 3F, 3G:
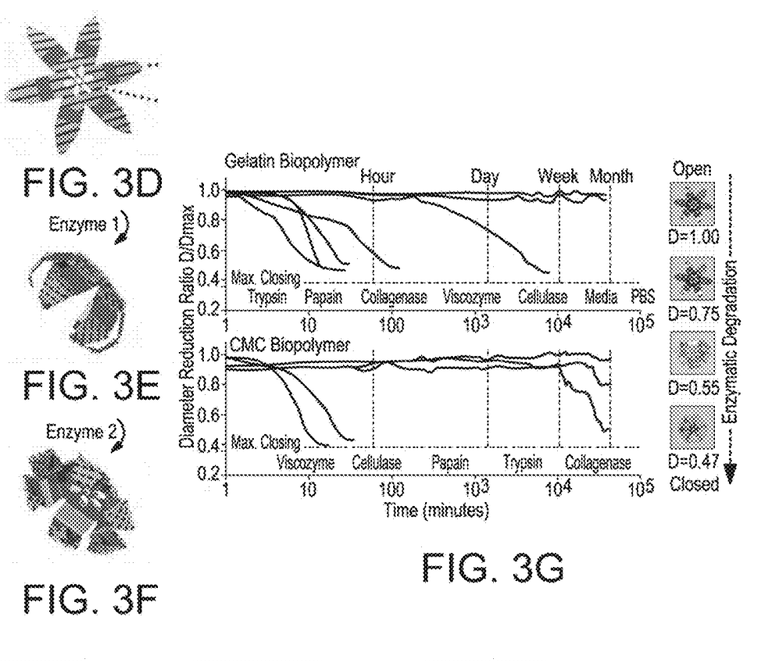
FIG. 3D-3F are images showing conformational change of the microgrippers patterned with bio-polymers upon enzymatic degradation of biopolymer layers and closing/re-opening of the devices.
FIG. 3G is a graphical plot showing the kinetics of microgrippers patterned with bio-polymers closing upon exposure to different enzymes. The graphs plot experimentally measured diameter reduction ratio versus time on exposure to a variety of enzymes. The line denotes the average value measured over 5 trials and shaded region denotes the standard deviation.

In FIG. 2G, we show the response of the tools to different hydrolytic enzymes. Using optical microscopy, the diameter (D) of grippers exposed to different enzymes was recorded over time. The parameter D/Dmax, was utilized which allowed quantification of closing and re-opening in various enzymes, and plot average data for 5 grippers. Open grippers at maximum spread have a defined edge-to-edge ratio D/Dmax of 1, and in this specific design, completely closed grippers have a theoretical minimum ratio of 0.355. As an example, it was experimentally observed that polypeptide grippers in trypsin fold to 90% of maximum (D/Dmax=0.42) in approximately 10 minutes.

It was observed that none of the grippers closed in the presence of PBS or mammalian cell media over 60 days. Upon addition of proteases such as trypsin, collagenase, or papain, sufficient degradation of the gelatin results in closing within 30 minutes. Proteases did not degrade the polysaccharide layers for a minimum of 30 days. After several weeks, some specificity was lost, as polypeptide grippers closed in cellulase in one week, and several polysaccharide grippers closed in papain at one month. This observation is attributed to the use of crude enzyme extracts from plant and bacterial sources that likely mixed protease/polysaccharidase activity.

Sensitivity of the grippers to decreasing concentrations of enzyme activity was also examined. Serial dilutions of collagenase were taken covering three orders of magnitude (5400 Units/mL to 21 Units/mL) and incubated UV sterilized gelatin grippers in the solutions. While the grippers in the highest concentrations closed in minutes, they took several weeks to close in the lowest enzyme concentrations. Similarly, CMC grippers exposed to a 2250 Unit/mL cellulase solution closed in under 5 minutes as compared to approximately 18 hours in a 27 Unit/mL dilution. Decreased enzyme activity is expected to increase closing time as both bond cleavage and diffusion will be reduced. However, the ability to actuate in varying enzyme concentrations suggests possible activity in vivo.

The gripper actuation was sensitive to the appropriate enzyme class for rapid actuation. This allowed a time window for differential actuation of orthogonal enzymes. Actuation of hinges in series was demonstrated by placing the grippers in solutions of papain and then cellulase, or vice versa. Orthogonal actuation of specific grippers was observed in only the corresponding enzymes.

The enzymatically triggered grippers were used to demonstrate medically relevant tasks. It is difficult to reach closed lumina in the body, such as the biliary tree, with tethered tools. One alternative is to manipulate untethered devices using magnetic forces, also permitting visualization via magnetic resonance imaging. CMC-gelatin grippers that could be closed and re-opened were used to securely grip a 700 μm alginate bead. Closing was actuated using a cellulase trigger. The gripper with the bead securely in its grasp was moved using a magnetic stylus and subsequently release the bead using a collagenase trigger. This demonstration highlights possible applicability in pick-and-place operations and on-demand drug delivery.

Avian liver tissue was biopsied from a model organ (cast from acrylic resin) with size scales approximately that of an adult human. For this experiment we utilized CMC grippers that closed in response to cellulase. After placing the grippers in the duodenum, they were remotely piloted them through the ampulla of Vater, through the common bile duct (5 mm diameter lumen), and into the liver. Cellulase solution was then added via syringe and the gripper closed around the tissue. Magnetic manipulation was used to extract the gripper and excised tissue, which was then stained (data not shown).

Additionally, the ability of these tools to retrieve cells for further diagnostic analysis was tested. A line of normal, SV-40 transformed, bile duct cells (H69) and a line of cholangiocarcinoma cells (HuCCT1) were cultured. After collecting the cells in a pellet CMC triggered grippers were introduced and closed them with cellulase (data not shown). The force exerted by an external magnet used to move the grippers was sufficient to hold up a large (9 mm) cell clump with eight grippers. Both cell types were analyzed via gel to confirm the presence of RNA (data not shown). This technique suggests that collection of clinically relevant data from gripper biopsy is feasible.

In conclusion, grippers triggered by specific enzyme substrate interactions have been demonstrated. These hybrid metal/polymer tools allow creation of miniaturized devices and materials that respond autonomously to specific biochemicals and disease markers. For example, by matching the biopolymer to proteolytic enzymes that are naturally secreted from cancer cells it should be possible to facilitate a tool that responds only to cancerous environments. It should also be possible to delay actuation by crosslinking protease inhibitors into the biopolymer or accelerate it using protease zymogens such as trypsinogen. Such methodology may be extended to other enzyme-biopolymer pairs such as the degradation of DNA based biopolymers using nucleases. In principle, the process is also compatible with nanoscale patterning techniques such as electron beam or direct write techniques which suggests the possibility of further miniaturization.

Although the invention has been described with reference to the above example, it will be understood that modifications and variations are encompassed within the spirit and scope of the invention. Accordingly, the invention is limited only by the following claims.

What is claimed is:

1. A method of tissue sampling comprising:
   a) introducing a system into a cavity of a subject, the system comprising:
      i) a device having an elongated tubular shaft having proximal and distal ends; and an inflatable balloon disposed on the distal end of the shaft, the inflatable balloon having one or more magnets disposed thereon and configured for retrieval or deployment of a plurality of tetherless microtools, wherein the shaft has one or more openings disposed proximal to the balloon for deployment of the plurality of tetherless microtools from a lumen of the shaft; and
      ii) a plurality of tetherless microtools magnetically detachable to the one or more magnets; and
   b) contacting the plurality of tetherless microtools with a tissue of the subject, each microtool having a first configuration;
   c) allowing the plurality of tetherless microtools to alter from the first configuration to a second configuration while in contact with the tissue, the second configuration adapted such that each microtool grasps the tissue at a discrete location; and
   d) retrieving the plurality of tetherless microtools from the subject using the one or more magnets, wherein each microtool retains an individual sample of the tissue upon retrieval, thereby performing tissue sampling.

2. The method of claim 1, wherein the device is configured as a balloon catheter having an elongated shaft of circular cross-sectional shape having proximal and distal ends.

3. The method of claim 1, wherein the plurality of tetherless microtools includes between about 2-1000, 2-500, 2-250, 2-100 or 10-100 microtools.

4. The method of claim 1, further comprising analyzing the individual samples retrieved from the plurality of tetherless microtools.

5. The method of claim 1, wherein a randomized statistical sampling is provided.

6. A method for retrieval of a tetherless microtool from a subject comprising:
   a) introducing a device into a cavity of the subject, the cavity having a tetherless microtool attached thereto, wherein the device has an elongated tubular shaft having proximal and distal ends; and an inflatable balloon disposed on the distal end of the shaft, the inflatable balloon having one or more magnets disposed thereon and configured for retrieval or deployment of a plurality of tetherless microtools, wherein the shaft has one or more openings disposed proximal to the balloon for deployment of the plurality of tetherless microtools from a lumen of the shaft;
   b) allowing the one or more magnets of the device to contact the tetherless microtool; and
   c) retrieving the tetherless microtool from the subject via magnetism by removing the device from the cavity, wherein the microtool retains a tissue sample from the cavity upon retrieval.

7. A method of diagnosing a condition or disease in a subject comprising:
   a) obtaining a tissue sample from a subject via the method of claim 1;
   b) analyzing the tissue sample; and
   c) providing a diagnosis of the condition or disease based on the analysis of the tissue sample.

8. A method of providing a prognosis for a condition or disease in a subject comprising:
   a) obtaining a tissue sample from a subject via the method of claim 1;
   b) analyzing the tissue sample; and
   c) providing a prognosis of the condition or disease based on the analysis of the tissue sample.

* * * * *